United States Patent
Horn et al.

(10) Patent No.: US 12,042,661 B2
(45) Date of Patent: Jul. 23, 2024

(54) METHODS AND SYSTEMS FOR GENERATING A TISSUE POCKET IN A PATIENT

(71) Applicants: Cook Biotech Incorporated, West Lafayette, IN (US); Cook Medical Technologies LLC, Bloomington, IN (US)

(72) Inventors: Joseph B. Horn, Boulder, CO (US); Michael C. Hiles, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 0 days.

(21) Appl. No.: 13/755,129

(22) Filed: Jan. 31, 2013

(65) Prior Publication Data

US 2013/0144356 A1  Jun. 6, 2013

Related U.S. Application Data

(63) Continuation of application No. PCT/US2011/045835, filed on Jul. 29, 2011.
(Continued)

(51) Int. Cl.
*A61N 1/375* (2006.01)
*A61L 27/36* (2006.01)
(Continued)

(52) U.S. Cl.
CPC .......... *A61N 1/375* (2013.01); *A61L 27/3633* (2013.01); *A61L 27/3808* (2013.01);
(Continued)

(58) Field of Classification Search
CPC ............................ A61N 1/375; A61L 27/3633
(Continued)

(56) References Cited

U.S. PATENT DOCUMENTS 1,798,945 A * 3/1931 Lamarthe ............... A45C 13/06
24/30.5 R
4,902,508 A   2/1990 Badylak et al.
(Continued)

FOREIGN PATENT DOCUMENTS

WO   WO 2005/097219   10/2005

OTHER PUBLICATIONS

Badylak, Stephen, "Xenogeneic Extracellular Matrix as a Scaffold for Tissue Reconstruction", Transplant Immunology, vol. 12, pp. 367-377.

*Primary Examiner* — William J Levicky
(74) *Attorney, Agent, or Firm* — Woodard Emhardt Henry Reeves & Wagner (57) ABSTRACT

Certain aspects of this disclosure relate to uniquely constructed medical implants that incorporate an electronic or other medical device. Some illustrative pocket-like implants provide an interior space for receipt of an electronic medical device, and are implantable in a patient with the electronic medical device positioned in the interior space. In one form, an inventive construct includes a remodelable material component that is effective upon implantation to promote cellular invasion and ingrowth into the remodelable material so that it becomes replaced by new patient tissue and so that the electronic medical device becomes surrounded by a new pocket structure comprised of newly generated, functional patient tissue. The electronic medical device will be a pacing device or other cardiac rhythm management (CRM) device in select embodiments.

15 Claims, 2 Drawing Sheets

Related U.S. Application Data (60) Provisional application No. 61/369,691, filed on Jul. 31, 2010.

(51) Int. Cl.
    *A61L 27/38*     (2006.01)
    *A61L 27/54*     (2006.01)
    *A61L 27/58*     (2006.01)
    *A61N 1/362*     (2006.01)

(52) U.S. Cl.
    CPC ............... *A61L 27/54* (2013.01); *A61L 27/58* (2013.01); *A61N 1/3629* (2017.08); *A61N 1/37512* (2017.08); *A61L 2430/20* (2013.01)

(58) Field of Classification Search
    USPC .......................................................... 607/36
    See application file for complete search history.

(56) References Cited

U.S. PATENT DOCUMENTS

| | | | |
|---|---|---|---|
| 5,275,826 A | 1/1994 | Badylak et al. | |
| 5,281,422 A | 1/1994 | Badylak et al. | |
| 5,352,463 A | 10/1994 | Badylak et al. | |
| 5,480,424 A | 1/1996 | Cox | |
| 5,554,389 A | 9/1996 | Badylak et al. | |
| 5,733,337 A | 3/1998 | Carr, Jr. et al. | |
| 6,206,931 B1 | 3/2001 | Cook et al. | |
| 6,358,284 B1 | 3/2002 | Fearnot et al. | |
| 6,379,710 B1 | 4/2002 | Badylak | |
| 6,719,788 B2 | 4/2004 | Cox | |
| 7,033,611 B2 | 4/2006 | Lyngstadaas et al. | |
| 7,244,444 B2 | 7/2007 | Bates | |
| 7,550,004 B2 | 6/2009 | Bahler et al. | |
| 7,981,065 B2* | 7/2011 | Westlund ............. A61N 1/0587 601/136 |
| 8,758,448 B2* | 6/2014 | Matheny .................... 623/23.72 |
| 8,980,296 B2 | 3/2015 | Matheny et al. | |
| 9,010,444 B2 | 4/2015 | Quitberg | |
| 9,044,319 B2 | 6/2015 | Matheny | |
| 9,072,816 B2 | 7/2015 | Matheny | |
| 2003/0036797 A1 | 2/2003 | Malaviya et al. | |
| 2004/0243222 A1* | 12/2004 | Osborne ............... A61F 2/2418 623/1.24 |
| 2005/0013870 A1 | 1/2005 | Freyman et al. | |
| 2005/0181016 A1 | 8/2005 | Freyman et al. | |
| 2006/0039896 A1* | 2/2006 | Kleinsek ............. A61L 27/3633 424/93.7 |
| 2006/0134079 A1* | 6/2006 | Sih ......................... A61N 1/375 607/2 |
| 2006/0136027 A1* | 6/2006 | Westlund ............. A61N 1/0587 607/123 |
| 2006/0136028 A1 | 6/2006 | Ross et al. | |
| 2006/0147492 A1 | 7/2006 | Hunter et al. | |
| 2006/0161265 A1* | 7/2006 | Levine ................ A61B 17/1114 623/1.36 |
| 2006/0201996 A1 | 9/2006 | Hodde | |
| 2006/0204738 A1* | 9/2006 | Dubrow .................. A61L 27/34 428/292.1 |
| 2006/0206139 A1* | 9/2006 | Tekulve ........... A61B 17/12131 606/200 |
| 2006/0229670 A1 | 10/2006 | Bates | |
| 2007/0014868 A1 | 1/2007 | Matheny | |
| 2007/0014869 A1 | 1/2007 | Matheny | |
| 2007/0014870 A1 | 1/2007 | Matheny | |
| 2007/0014871 A1 | 1/2007 | Matheny | |
| 2007/0014872 A1 | 1/2007 | Matheny et al. | |
| 2007/0014873 A1 | 1/2007 | Matheny | |
| 2007/0014874 A1 | 1/2007 | Matheny | |
| 2007/0168021 A1 | 7/2007 | Holmes et al. | |
| 2008/0132922 A1* | 6/2008 | Buevich ............. A61N 1/37512 606/151 |
| 2008/0199507 A1* | 8/2008 | Skarja .................. A61K 9/0024 424/423 |
| 2008/0274184 A1 | 11/2008 | Hunt | |
| 2008/0281418 A1 | 11/2008 | Firestone | |
| 2009/0138074 A1* | 5/2009 | Freyman ............. A61L 27/3633 623/1.38 |
| 2010/0028396 A1 | 2/2010 | Ward et al. | |
| 2010/0030292 A1* | 2/2010 | Sarkar et al. ...................... 607/6 |
| 2010/0047305 A1 | 2/2010 | Naughton et al. | |
| 2010/0168808 A1* | 7/2010 | Citron .................... A61L 31/10 607/5 |
| 2010/0233235 A1 | 9/2010 | Mathney | |
| 2010/0262221 A1* | 10/2010 | Schafer et al. .............. 623/1.13 |
| 2012/0034191 A1 | 2/2012 | Matheny et al. | |
| 2012/0156255 A1 | 6/2012 | Singh et al. | |
| 2012/0302499 A1 | 11/2012 | Matheny | |
| 2013/0023721 A1* | 1/2013 | Matheny ......................... 600/16 |
| 2013/0202563 A1 | 8/2013 | Badylak et al. | |
| 2016/0008514 A1* | 1/2016 | Jones .................... A61L 27/362 424/423 |
| 2022/0047777 A1* | 2/2022 | Zhang ................. A61L 27/3633 |

\* cited by examiner

METHODS AND SYSTEMS FOR GENERATING A TISSUE POCKET IN A PATIENT

REFERENCE TO RELATED APPLICATIONS

This application is a continuation of International Application No. PCT/US2011/045835, filed Jul. 29, 2011, pending, which claimed the benefit of U.S. Provisional Patent Application No. 61/369,691, filed Jul. 31, 2010, abandoned, entitled METHODS AND SYSTEMS FOR GENERATING A TISSUE POCKET IN A PATIENT, both of which are incorporated herein in their entirety.

BACKGROUND

The present invention relates generally to medical devices and in particular aspects to methods and systems for generating a natural tissue pocket in a patient for example to contain an implant such as a pacemaker or defibrillator.

As further background, the medical industry has developed a variety of implantable devices and systems for sensing and/or affecting bodily function upon implantation and/or for carrying out various other functions in the body. These include but are not limited to pacing devices, defibrillators, implantable access systems, monitors, stimulators including neurostimulators, ventricular assist devices, pain pumps, infusion pumps and other implantable objects or systems or components thereof, for example, those used to deliver energy and/or substances to the body and/or to help monitor bodily function.

Typically, cardiac pacing by an artificial pacemaker delivers a stimulus to the heart when its own natural pacemaker and/or conduction system fails to provide synchronized atrial and ventricular contractions at desirable rates and intervals. Such pacing provides relief from symptoms and even life support for hundreds of thousands of patients.

Cardiac pacing is usually performed by a pulse generator implanted subcutaneously or sub-muscularly in or near a patient's pectoral or abdominal region. The generator usually connects to the proximal end of one or more implanted leads, the distal end of which contains one or more electrodes to be positioned at one or more cardiac locations.

There remain needs for improved and/or alternative products to promote and/or facilitate the successful implantation of medical devices and systems in the body, as well as methods for preparing and utilizing such products. The present invention, in certain embodiments, is addressed to those needs.

SUMMARY

The present invention provides, in certain aspects, unique medical implants that incorporate a cardiac rhythm management (CRM) device or other implantable medical device. Some inventive implant systems include an implantable pocket and a CRM device positioned in the pocket. The pocket incorporates a remodelable material, and is implantable in the patient with the CRM device positioned in the pocket. Following implantation, cells invade the remodelable material eventually leading to the generation of a new pocket structure around the CRM device that comprises newly remodeled, functional tissue of the patient. The remodelable material of the implantable pocket and the surface of the CRM device can be selected such that upon remodeling of the pocket, newly generated patient tissue does not become fused or adhered to or infiltrated into the surface of the CRM device.

In another embodiment, the invention provides a method of treating a patient that includes providing a collagenous material pocket implanted within a patient with an implantable electronic medical device positioned in the pocket. The pocket includes endothelial cells present on an interior surface of the pocket.

One aspect of the present invention provides a method of treating a patient that includes providing a remodelable material pocket implanted within a patient with an implantable medical device positioned in the pocket. The remodelable material is effective to promote cellular invasion and ingrowth into the remodelable material such that the medical device will become at least partially surrounded by remodeled patient tissue following implantation.

Another aspect of the invention provides an implantable pocket for use with a medical device that is dimensioned for slidable receipt within the pocket. The pocket has a plurality of closed sides and an open side that is dimensioned for slidable entrance of the medical device. The pocket is formed with a remodelable extracellular matrix material that has been harvested from a collagenous tissue source and that is effective to promote cellular invasion and ingrowth into the remodelable material such that the medical device will become at least partially surrounded by remodeled patient tissue following implantation.

A further embodiment of the invention provides a method of treating a patient that includes creating an opening in the skin of a patient so as to provide access to subcutaneous body location. Thereafter, a remodelable extracellular matrix sheet material, which provides an initial pocket structure for receipt of an implantable electronic medical device, is placed in the body location. Also in this method, an implantable electronic medical device is placed in the initial pocket structure. The remodelable extracellular matrix sheet material is effective upon implantation to promote cellular invasion and ingrowth into the remodelable extracellular matrix sheet material so that the initial pocket structure becomes replaced by new patient tissue and thereby provides a remodeled tissue structure at least partially surrounding the medical device in the body location.

Yet another embodiment of the invention involves placing an electronic medical device at an implant site so that it is at least partially surrounded by an initial covering or shielding-type structure. The covering is fully remodelable or at least incorporates a remodelable material. As the remodelable material remodels, it breaks down and becomes replaced by new patient tissue so that eventually a new covering or shield-type structure that comprises newly generated, functional patient tissue surrounds the electronic device, in whole or in part, at the implant site.

Still another embodiment of the invention provides a method for generating a pocket tissue structure in soft tissue of a patient. The method includes implanting in soft tissue of the patient a pocket construct comprising a remodelable material, the pocket construct containing a medical implant having an outer surface that is non-receptive to tissue ingrowth. The remodelable material is effective upon implantation to become replaced by new patient tissue so that a remodeled tissue pocket structure comprising new patient tissue is generated around the medical implant. The medical implant can for example be any of those described herein. Alternatively the medical implant can be an initial space-occupying implant which, after generation of the remodeled tissue pocket, can be surgically removed and replaced by another implantable medical device as described herein or otherwise.

Additionally, uses of remodelable materials in the manufacture of medical products for providing pockets into which implantable medical devices can be positioned in the body of a patient are provided by certain aspects of the present invention. Such remodelable materials are effective to promote cellular invasion and ingrowth into the pockets such that the implantable medical devices will become at least partially surrounded by remodeled patient tissue following implantation. In some forms, these remodelable materials will be remodelable collagenous extracellular matrix materials such as those obtained in sheet or other forms from mammalian tissue sources.

Other objects, embodiments, forms, features, advantages, aspects, and benefits of the present invention shall become apparent from the detailed description and drawings included herein.

DETAILED DESCRIPTION

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique implants that incorporate an electronic or other implantable medical device. One illustrative pocket-like implant provides an interior space for receipt of an electronic medical device, and is implantable in a patient with the electronic medical device positioned in the interior space. This particular implantable construct includes a remodelable material component that is effective upon implantation to promote cellular invasion and ingrowth into the remodelable material so that it becomes replaced by new patient tissue and so that the electronic medical device becomes surrounded by a new pocket structure comprised of newly generated, functional patient tissue. In some instances, essentially the entire construct housing the electronic device will be formed with remodelable material. In other instances, a remodelable material component will be combined with at least one non-remodelable component such as a resorbable or non-resorbable liner, inner and/or outer reinforcing material, fill material or other non-remodelable component as described elsewhere herein. The electronic medical device will be a pacing device or other cardiac rhythm management (CRM) device in some embodiments. The present invention also provides methods for preparing and utilizing these and other implantable structures, as well as medical products that include such implantable structures enclosed within sterile packaging.

Turning now to a more detailed discussion of materials that can be utilized in the present invention, particular advantage will be provided by inventive constructs that incorporate a remodelable material. Such remodelable materials can be provided by collagenous materials, e.g., provided in a reconstituted or non-reconstituted form, obtained from a warm-blooded vertebrate, and especially a mammal. Isolated collagenous materials can be processed so as to have remodelable, angiogenic properties and promote cellular invasion and ingrowth, and in this regard, inventive constructs comprising a remodelable material and containing an electronic implantable medical device can be effective upon implantation to stimulate ingrowth of adjacent tissues into the construct such that the remodelable material gradually breaks down and becomes replaced by new patient tissue so that a new, remodeled tissue structure is generated forming a patient tissue pouch around the IMD or other device. With such products, the functionality of the pocket is maintained throughout the remodeling process so that the IMD will continue to be surrounded by a functional and device-friendly pocket or pocket-like structure as the remodeling occurs.

Suitable remodelable materials can be provided by collagenous extracellular matrix (ECM) materials. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. Collagenous matrices that are quite pliable so as to be easily conformable to the IMD will be useful in certain aspects of the invention. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Remodelable ECM tissue materials harvested as intact sheets from a mammalian source and processed to remove cellular debris advantageously retain at least a portion of and potentially all of the native collagen microarchitecture of the source extracellular matrix. This matrix of collagen fibers provides a scaffold to facilitate and support tissue ingrowth, particularly in bioactive ECM implant materials, such as porcine small intestinal submucosa or SIS (Surgisis® Biodesign™, Cook Medical, Bloomington Ind.), that are processed to retain an effective level of growth factors and other bioactive constituents from the source tissue. In this regard, when an inventive construct incorporates this sort of material, cells will invade the remodelable material upon implantation eventually leading to the generation of a newly-remodeled, functional tissue structure, for example, providing at least part of a pocket or pocket-like structure around a pacemaker or other implantable medical device (IMD). In some forms, the generated structure will provide a remodeled tissue wall that covers at least part of the medical device. Remodeled, organized tissue layers, when formed, can conform to an IMD to provide a secure, fitted placement of the IMD at the implant site.

Inventive implants place the IMD in a considerably more device-friendly environment as compared to other products, for example, by actually generating a new, highly functional tissue structure around the IMD. With other, persistent synthetic polymer products, the foreign body (i.e., the IMD or the non-degradable structure containing the IMD) can become encapsulated and sometimes adversely deformed by solely non-functional, rigid, fibrotic scar tissue which can be problematic for a number of reasons. For one, the rigid non-functional tissue and potentially deformations of the non-degradable containment structure can be irritating to the patient, and can otherwise be a source of discomfort and distraction. Also, this sort of rigid and uncontrolled fibrotic scar tissue can be much more difficult and dangerous to manage should the IMD ever need to be explanted or accessed for any reason, for example, to replace a battery or to perform maintenance on the device. Further, rigid and uncontrolled scarring can damage or otherwise undesirably interfere with accessories positioned in and/or around the implant. For example, if there are leads or other components extending from the structure, they might get damaged as uncontrolled fibrosis occurs around the implant, for example, by getting bent, twisted, pulled and/or bound up in the fibrotic tissue.

With inventive constructs, it is possible in some aspects to generate highly-functional and organized tissue structures around an IMD, to reduce the amount of total scar tissue occurring around the implant, to keep unremodeled encapsulating scar tissue from contacting the IMD, and/or to better predict and manage the type(s) of growth occurring in and/or around the implant and/or any components or accessories associated with the implant, among other things. In certain embodiments, it will be possible to temporarily access the generated remodeled patient tissue pouch or even replace an IMD without removing while leaving he remodeled pouch intact.

Figure 1:
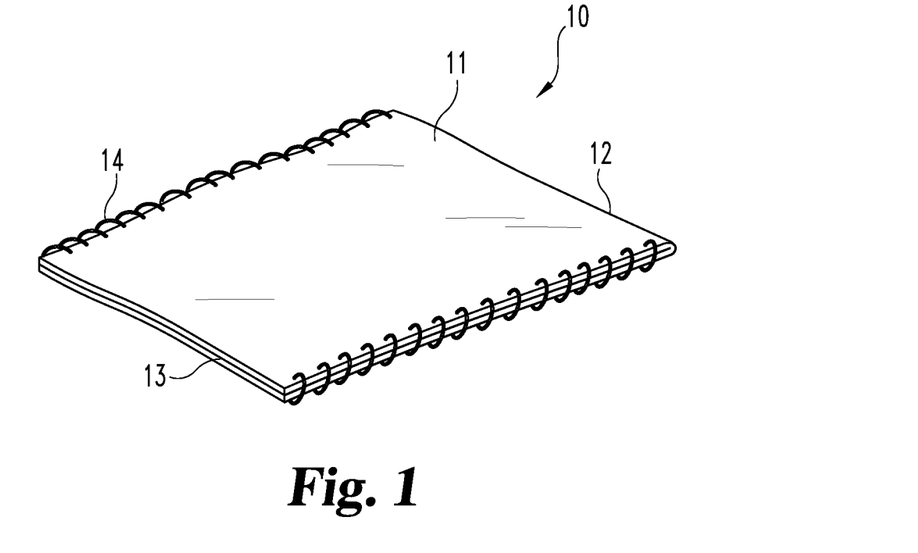
FIG. 1 is a perspective view of a medical product according to one embodiment of the present invention.

With reference now to FIG. 1, shown is an implantable pocket structure 10 according to one embodiment of the present invention. Pocket structure 10 includes a folded segment 11 of a remodelable ECM material such as single- or multilayered porcine small intestinal submucosal or other ECM material. The segment 11 can be formed with one or more individual pieces of material, and it is initially about twice as long as structure 10 so that it can be folded over itself to provide a folded, closed end 12 opposite an open end 13 as shown. Opposing sides 14 are also formed by this process and in this particular embodiment they are thereafter closed off with biodegradable sutures 14 although a variety of other closing adaptations can be employed as will be recognized by those skilled in the art. With this sort of construction, open end 13 will communicate with an interior space that is dimensioned for slidable receipt of an electronic or other implantable medical device such as a pacing device or other cardiac rhythm management (CRM) device. In this regard, the interior space is located between a top layer and a bottom layer of the implantable pocket structure 10. With the CRM device positioned in the pocket, optionally the open end 13 can be closed off as well as part of the process. In certain embodiments, a closure flap extending over and generally closing the open end 13 can be used for this purpose, and can have, or can be cut at the time of surgery to have, one or more exit openings for passage of leads from the CRM or another electronic device out of the pocket structure 10.

Although inventive pockets and other structures can be formed with a variety of materials, in certain instances, essentially the entire structure will be formed with a remodelable material such that the IMD will eventually reside in an all-natural, functional tissue pocket that was generated in the patient after the initial, remodelable structure was implanted. Still, in some embodiments, a pocket or pocket-like structure that includes a remodelable material will also incorporate a non-remodelable component. Illustratively, a composite pocket structure might include a non-remodelable lining, layer, wall, filler, reinforcement, framework, or other structural or non-structural component in combination with a remodelable material. Illustratively, a remodelable component might include one or more layers of remodelable material, and a non-remodelable component might be located to one or both sides of a remodelable layer, and potentially between adjacent remodelable layers if more than one remodelable layer is present in the implant. In some inventive composite structures, a remodelable material will be interwoven with a non-remodelable material to form an implantable structure with in interior region for receipt of an IMD or other medical device.

A pocket or other inventive structure that is to contain a pacemaker or other IMD can be constructed so that the structure, or any portion thereof, has a tendency to contract or shrink somewhat after it is implanted in the body due to the remodeling process. In this regard, dimensions of an initial pocket structure can be made somewhat oversized so that it can easily accommodate the IMD and any accessories (e.g., excess leads) that might be placed in the pocket prior to and/or during the implantation procedure. This might be helpful to provide some extra room or void space in the pocket structure for initially holding the desired contents. Then, following the implantation and during remodeling, material of the pocket structure will contract somewhat around the IMD to reduce the available void space in the pocket and thereby provide a more snug fit of the IMD, or any portions thereof including any accessories that might be present, in the pocket structure. Following implantation, the percentage of available void space in the pocket structure can decrease, e.g. by at least 10%, including decreasing to eliminate essentially all of the available void space. When utilized in the present invention, materials that have a tendency to shirk or contract somewhat after implantation can be chosen from naturally derived or non-naturally derived materials, for example, fully or partially synthetic materials that are configured to shrink somewhat after being implanted. In certain aspects of the invention, remodelable ECM or other materials will be used which have the ability to contract or shrink as they are remodeled in the body following implantation.

Optionally, one or more materials or substances can be introduced into any void spaces in a construct and/or into the ECM and/or other material of the construct prior to completing an implantation procedure. These include but are not limited to fill materials such as remodelable or resorbable fill materials or other substances (e.g., in the form of fluids, pastes, gels, sponges, powders, tissue fragments, segments, strips, layers, etc.), therapeutic agents, e.g. any drug such as an antibiotic agent, antimicrobial agent, or the like as discussed elsewhere herein. As well, the exterior and/or interior of an inventive implantable construct can be coated with and/or the material of the construct can incorporate one or more of these materials or substances or another drug coating, either as-manufactured or by an attending health care provider at the point of surgery.

In some embodiments, an inventive pocket structure will be constructed so as to include an interior lining. A lining of this sort can include one or more of a variety of naturally derived and/or non-naturally derived materials and substances, and can be provided in a number of forms including but not limited to layers, reinforcements, frameworks, coating materials including bioactive substances, drugs, cells, etc. In some forms, an inventive structure will include a sheet or sheet-like material that lines all or part of an inventive pocket or pocket-like structure, for example, a resorbable or non-resorbable synthetic material liner. As well, these same materials and substances can be used to coat or otherwise provide an exterior surface of an inventive construct.

In certain embodiments of the present invention, endothelial cells are seeded on surfaces of the interior of the pocket, for example to promote the formation of an endothelialized inner surface of the remodeled patient tissue structure. Illustratively, endothelialized tissue can be obtained and used to line the interior of an inventive pocket structure as described herein. Alternatively, a preselected population of endothelial cells can be added to a substantially acellular biomaterial such as an extracellular matrix material of any type described herein, for example, by harvesting small patches of endothelial cells directly from a donor tissue (e.g. a vessel of the patient to be treated, or a cadaver) and seeding them onto an extracellular matrix surface whereby they will attach and proliferate to cover the ECM surface. In this regard, a wall of material, which otherwise forms at least part of an interior surface of a pocket or pocket-like structure, can be lined with endothelial cells so that upon implantation an endothelialized pocket structure will be formed containing an electronic or other implantable medical device. Optionally, after a biomaterial has been seeded with endothelial cells, it can be subjected to conditions conducive to the proliferation of endothelial cells to further expand the population of the seeded cells prior to implantation in the patient.

Figure 2A:
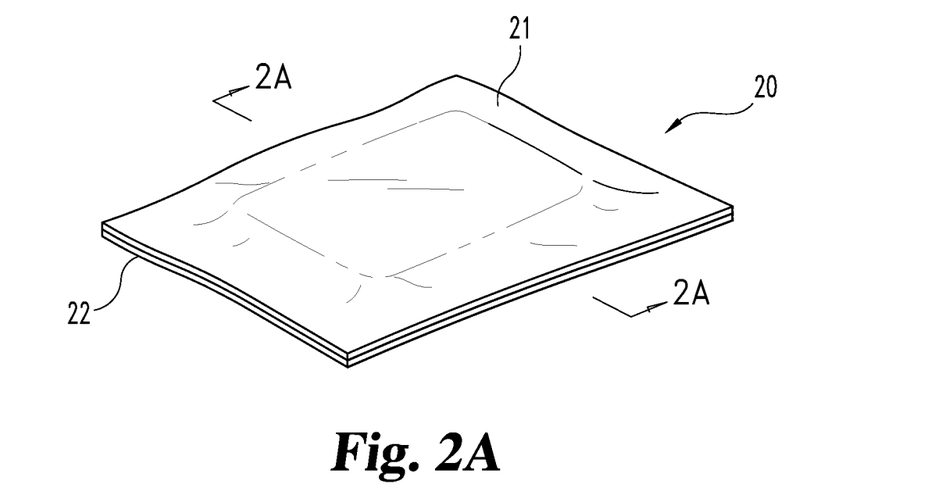
FIG. 2A is a perspective view of another inventive medical product.
Figure 2B:
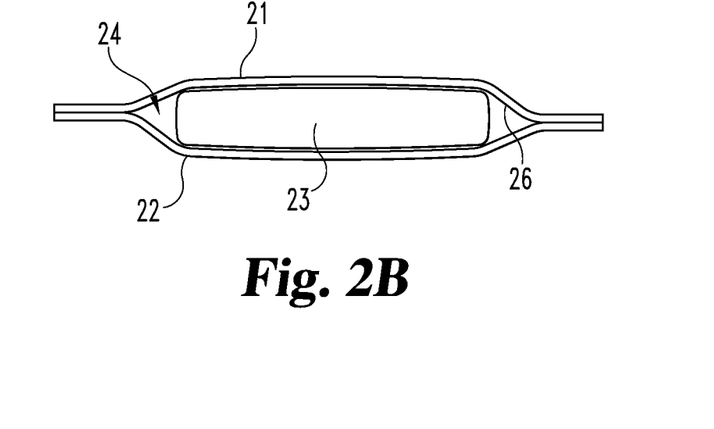
FIG. 2B provides a cross-sectional view of the medical product of FIG. 2A along the view line 2A-2A shown in FIG. 2A.

Referring now to FIG. 2A, shown is an implantable pocket structure 20 according to another embodiment of the present invention. Pocket structure 20 includes a top sheet or layer 21 and a bottom sheet or layer 22 that are both formed with a harvested remodelable ECM material. A CRM or other electronic device 23 (hidden in FIG. 2A) is positioned between the two sheets, and peripheral regions of the respective sheets are fused together to fully contain the CRM device between the two sheets. Contacting regions of a top and bottom layer can be fused together in any suitable manner including but not limited to using a bonding agent, compressing the regions under dehydrating conditions and/or using other fusing methods as described elsewhere herein, although sutures, staples or other binding mechanisms might additionally or alternatively be used as well. FIG. 2B is a cross-sectional view of pocket structure 20 along the view line 2A-2A shown in FIG. 2A. As can be seen, peripheral contacting regions of the top sheet 21 and bottom sheet 22 are fused together so that the CRM device 23 fits rather snugly between the sheets with some void space 24 occurring around the CRM device in the interior of the pocket. In an alternative arrangement, the top and bottom sheets are fused together in a rather tight manner so that essentially no void space occurs in the pocket interior around the CRM device. Also shown in FIG. 2B is an optional liner 26 that lines at least a portion of the interior of the pocket. In one specific illustrative embodiment, one or more layers of a biodegradable, synthetic material line the interior of the pocket, although many other types of lining substances and materials can be introduced as well as described elsewhere herein. Additionally, in certain embodiments, the pocket structure can be manufactured to have or cut at the time of surgery to have one or more exit openings for passage of leads from a CRM or another electronic device out of the pocket structure 10.

Figure 3:
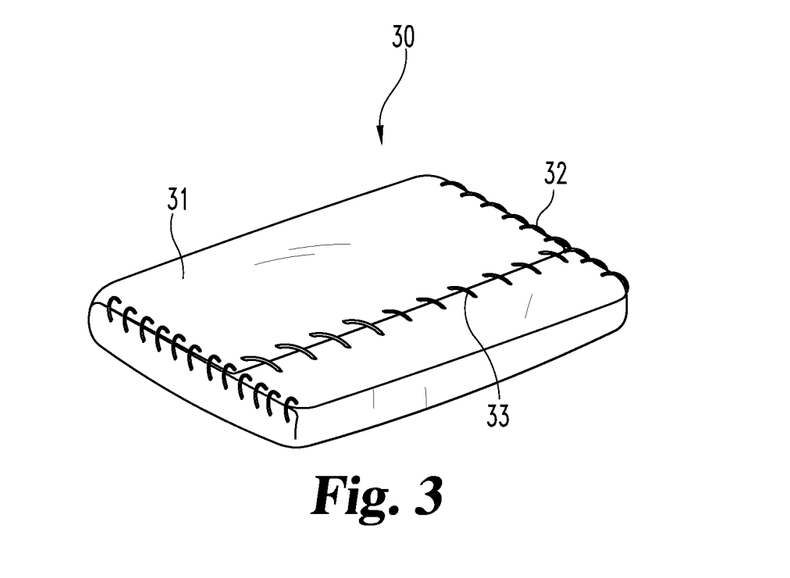
FIG. 3 is a perspective view of another inventive medical product.

Referring now to FIG. 3, shown is an implantable pocket structure 30 according to yet another embodiment of the present invention. Pocket structure 30 includes an implantable electronic medical device (hidden in FIG. 3) that is wrapped in a segment 31 of a remodelable ECM material. The segment 31 can be formed with one or more individual pieces of material that can be arranged around the electronic device in a variety of fashions. While not necessary to broader aspects of the invention, in this specific illustrative embodiment, two pieces of remodelable ECM material are combined such that the pocket structure has two lateral, end seams 32 and two longitudinal seams 33 (bottom, longitudinal seam hidden in FIG. 3). Various other seam arrangements are contemplated and may depend on the number and/or shapes of the material pieces used to form the construct. Biodegradable staples are used in this illustrative embodiment to hold the materials together although a variety of other closing adaptations can be employed as will be recognized by those skilled in the art. As well, as in other pocket constructs disclosed herein, the pocket can be manufactured to have or cut at the time of surgery to have one or more exit openings for passage of leads from a CRM or another electronic device out of the pocket structure 10.

Continuing with a discussion of materials that can be utilized in the present invention, submucosa-containing or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 μg/mg, more preferably less than about 2 μg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa-containing or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient. In certain embodiments, one or more antibiotic agents will be incorporated into ECM material included in the pocket construct, for example rifampin, minocycline, or a combination thereof. Alternatively or in addition, rifampin, minocycline, a combination thereof, and/or other antibiotic(s) can be incorporated in a bioabsorbable polymer coated on and/or incorporated within ECM material included in the pocket construct. The bioabsorbable polymer can be, for example, an bioabsorbable polymer identified herein, or any combination thereof.

Inventive devices can incorporate xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

When used in the invention, ECM materials may be essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue.

In this regard, any porous component of an inventive product (including any ECM material) can have a level or degree of porosity. In certain embodiments, the porosity of a layer of ECM material is lowered by drying the material under compression. In general, compressing a pliable open matrix material, such as a pliable ECM material, increases the material's bulk density and decreases the material's porosity by decreasing the size of the voids in the open matrix. As is the case in certain aspects of the invention, when such a material is dried while being compressed, particularly under vacuum pressing conditions, the open matrix structure can become somewhat fixed in this relatively higher bulk density, lower porosity state (i.e., in a relatively more collapsed state). It should be noted that different compressing and drying techniques and/or methods, including different degrees of compressing and drying, can be designed through routine experimentation so as to allow for a material layer having an optimal degree of material bulk density and/or porosity for a particular application or procedure.

Multilaminate structures when used in the invention can include a plurality of ECM material layers bonded together, a plurality of non-ECM material layers bonded together, or a combination of one or more ECM material layers and one or more non-ECM material layers bonded together. Illustratively, two or more ECM segments can be fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. A combination of one or more of these with dehydration-induced bonding may also be used to bond ECM material layers to one another.

A variety of dehydration-induced bonding methods can be used to fuse ECM portions together. In one preferred embodiment, multiple layers or other pieces of ECM material are compressed under dehydrating conditions. The term "dehydrating conditions" can include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressing surfaces. One particularly useful method of dehydration bonding ECM materials is lyophilization, e.g. freeze-drying or evaporative cooling conditions.

Another method of dehydration bonding comprises pulling a vacuum on the assembly while simultaneously pressing the assembly together. This method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is sometimes advantageous to perform drying operations under relatively mild temperature exposure conditions that minimize deleterious effects upon the ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

A sheet or sheet-like material when used in the invention can have one or more slit or non-slit openings that extend into and/or through the material, and these openings may be located in various regions of the material. In certain embodiments, it may be advantageous to process a sheet or layer, or any portion thereof, so that it exhibits a meshed structure. Illustratively, a meshed structure can have a plurality of slits therein to provide a mesh pattern, and the mesh pattern can be useful to provide deformability to the structure, and in some case, expandability. In this regard, in some meshed constructs, expansion or other deformation of the structure will widen the openings created by the slits of the mesh pattern, by lateral and/or vertical displacement of the edges of the slits relative to one another. Certain meshed devices of the invention will have a mesh pattern providing an expansion ratio of at least about 1.2:1 when the layer is completely hydrated, more preferably at least about 2:1, and most preferably at least about 3:1. Such highly deformable structures provide surprisingly beneficial properties to the structure, particularly in situations where deformability and/or expandability provide advantages.

A meshed pattern can be created using suitable meshing devices designed for processing skin autograft sections. Such devices can include a cylindrical drum cutter with a plurality of edges for providing the slit pattern of the mesh. A variety of such devices are known and can be used in the invention. For additional information as to meshers, reference may be made to U.S. Pat. Nos. 5,004,468, 6,063,094, 3,472,228, 3,358,688, and 3,640,279. These and other devices incorporating a meshing drum provide for a convenient, high-throughput method of preparing meshed material layers or constructs used in the invention. It will be understood, however, that the mesh pattern can be made by hand-cutting the material or by using appropriate cutting tools with multiple blades to cut the slits to provide the mesh pattern. While a meshed material layer, when utilized in the present invention, can form any suitable part of an inventive construct, in some forms, at least the outermost layer of the construct will be formed with a meshed material layer. Illustratively, a multilayered pocket or pocket-like structure might have an exterior layer formed with a meshed material, and an interior layer formed with a meshed or non-meshed material. In one embodiment, a pocket structure will have an interior liner formed with a non-meshed material and an exterior surface provided by a meshed material.

In some inventive constructs, a variety of synthetic polymeric materials including but not limited to bioresorbable and/or non-bioresorbable plastics may be used to provide one or more components of the construct. Bioresorbable, or bioabsorbable polymers that may be used include, but are not limited to, poly(L-lactic acid), polycaprolactone, poly (lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

As well, inventive constructs can incorporate biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

When constructed for use with electronic and other implantable medical devices, inventive pocket structures can be shaped and configured in a variety of manners to accommodate such devices. Pacemakers and defibrillators commonly form part of an inventive system, although various other implantable devices and components can be incorporated into or otherwise used in conjunction with the pocket-providing constructs described herein. Suitable devices include those used to sense and/or affect bodily function upon implantation and/or for carrying out various other functions in the body. These can be but are not limited to pacing devices, defibrillators, implantable access systems, monitors, stimulators including neurostimulators, ventricular assist devices, pain pumps, infusion pumps and other implantable objects or systems or components thereof, for example, those used to deliver energy and/or substances to the body and/or to help monitor bodily function. Accordingly, inventive products and systems can be implanted at a variety of locations in the body including many different subcutaneous and sub-muscular locations. The outer surfaces of the pacemaker, defibrillator or other implantable medical device can be made of metal or synthetic polymer, and can in certain embodiments be generally smooth and non-receptive to new tissue ingrowth. In this manner the regions of the inventive pocket constructs positioned adjacent to such outer surfaces can generate a new patient tissue pocket structure as discussed herein without causing adhesion of the new tissue to the implantable medical device. Also, as discussed elsewhere herein, inventive constructs, if desired, can be especially configured so that the remodelability characteristics of the device are optimized for the conditions expected at the particular implant location, for example, by performing one or more physical, chemical, biological and/or other manipulations to the remodelable material to account for variables such as the type(s) of tissue occurring at the implant site, the level of blood supply at the site and/or other site specific conditions regarding the implant site of choice.

Inventive structures providing a pocket or space for receiving such devices can be shaped and configured to hold, surround, receive, encapsulate, enclose, cover and/or encase such devices, fully or partially. Pockets and other inventive constructs can be designed to fit a wide range of implantable devices, systems and components thereof. In some instances, a construct will be sized to accommodate a specific device or group of devices from one or more manufacturers. In other instances, a more generic structure will be provided, and the end user will be able to easily modify the structure to accommodate a particular device prior to implantation.

As well, inventive constructs can be shaped and configured to accommodate any leads or other attachments or accessories which may be part of a device or system to be implanted. In this regard, an inventive construct might be provided with one or more openings in the body of the construct that would allow a lead or other similar component to extend from a location within a construct to a location exterior of the construct. Typically, leads are used for patient sensing and, in some cases, for both sensing and stimulation. For example, electrodes on implantable medical leads may detect electrical signals within a patient, such as an electrocardiogram, in addition to delivering electrical stimulation.

Typically, cardiac rhythm management devices (CRMs) are designed to deliver therapeutic stimulation to the heart, for example, in the form of pacing, cardioversion or defibrillation pulses. Such devices generally include a generator and one or more leads. The generator is typically placed below the skin in the chest area (e.g., over or near the breastbone). The generator typically houses a battery and a computer. Energy is stored in the battery until it is needed. The computer receives information on cardiac function via the leads and reacts to that information on the basis of its programming. The lead(s) extend from the generator to one or more cardiac locations.

An implantable cardioverter defibrillator typically includes one or more leads and a pulse generator. The lead(s) monitor the heart rhythm and deliver energy used for pacing and/or defibrillation. Different types of ICDs include but are not limited to single chamber ICDs, dual chamber ICDs, and biventricular ICDs.

A pacemaker can be used to maintain a suitable heart rate and rhythm. Sometimes pacemakers are used to treat fainting spells (syncope), congestive heart failure, hypertrophic cardiomyopathy and other conditions. Different types of pacemakers include but are not limited to single chamber pacemakers; dual chamber pacemakers; and biventricular pacemakers.

A large variety of devices capable of providing stimulation to one or more parts of the body can be used in accordance with the present invention, and in the regard, the targeted implant location for these devices will vary depending on the application. Neurostimulation, muscular stimulation, gastric stimulation and/or other stimulation can be administered via electrodes on the leads and located within or proximate to the target tissue, organ or other body part or system. As examples, implantable medical leads may be positioned proximate to the vagal nerve for delivery of neurostimulation to the vagal nerve. Implantable neurostimulators can be used to send a stimulus, e.g., an electrical signal, via leads to the spine or brain to treat pain and other neurological disorders. Gastrointestinal conditions, severe chronic nausea and vomiting as well as urological disorders can also be treated with appropriate devices as will be understood by those skilled in the art. Chronic pain including back, neck and spinal pain can be treated as well using known devices. Epilepsy and essential tremor including tremors associated with Parkinson's disease and other neurological disorders can be treated in accordance with the present invention. If drug or other delivery systems are used, they will typically include a pump and a catheter for dispensing the substances.

In one illustrative inventive method that involves the implantation of a pacemaker, for example, at a subcutaneous location near the breastbone, the skin above this area is disinfected and otherwise prepared. Thereafter, an incision is made in the skin, and a space for receiving an inventive pocket structure is made beneath the skin, for example, at a sub-muscular location. While the steps of this method can be performed in any suitable order, in some embodiments, the pocket will then be inserted into this space, and optionally secured to its surroundings. Next, the pacemaker is inserted into the pocket with any fillers, accessories, and/or other components also being placed in the pocket, around the pocket, and/or extending from the pocket. Optionally, the device and any accessories will be secured within the pocket and/or to other surroundings. If the pocket is of a type that can be closed, it may then be wholly or partially closed using sutures, staples or other single- or multiple-part closing mechanism, an adhesive and/or in any other suitable manner, being sure to desirably position and otherwise manage any leads or other accessories which might be present. When all parts of the system are desirably positioned in the body, the incision is closed.

Additionally, in certain embodiments, implants of the invention can incorporate an effective amount of one or more antimicrobial agents or agents otherwise useful to inhibit the population of the construct or surrounding tissue with bacteria or other deleterious microorganisms. Illustrative such agents can include, for example, silver compounds, such as silver salts (e.g. silver sulfate), dextran, chitosan, chlorhexidine, rifampin, minocycline, and/or nitric oxide donor compounds. In illustrative embodiments, such an agent or agents can be incorporated throughout the constructs and/or on surfaces and/or selected regions thereof. These or other similar therapeutic agents, e.g. any drug, such as an antibiotic, can be incorporated directly on or in the constructs of the invention, or they can be incorporated with a suitable binder or carrier material, including for instance hydrogel materials. In this regard, the construct can serve to release the one or more agents over time so as to treat the area during healing.

Turning now to a discussion of fill materials useful in some aspects of the invention, a void space in an implantable construct and/or around the construct upon implantation, can be filled with a fill material or other substance. In this regard, the fill material may be a solid, liquid, gel or foam, such as polymer, a remodelable or bioabsorbable material, saline, a non-bioabsorbable material, collagen rods or particulates, a collagenous or gelatinous foam, gelatin, oxidized regenerated cellulose, or any suitable combination thereof.

In one embodiment, a fill material will comprise a comminuted, fluidized, and/or gelatinous remodelable material. For example, a remodelable gel can be formed from fluidized compositions, as illustrated in U.S. Pat. Nos. 5,275,826, 5,516,533, 6,206,931, and/or International Publication No. WO2005020847 (Cook Biotech Incorporated) published Mar. 10, 2005, which are each hereby incorporated by reference in their entirety. In this regard, solutions or suspensions of ECM can be prepared by comminuting and/or digesting ECM with a protease (e.g. trypsin or pepsin), for a period of time sufficient to solubilize the ECM and form substantially a homogenous solution. The ECM starting material is desirably comminuted by tearing, cutting, grinding, shearing or the like. Grinding the ECM in a frozen or freeze-dried state is advantageous, although good results can be obtained as well by subjecting a suspension of pieces of the submucosa to treatment in a high speed blender and dewatering, if necessary, by centrifuging and decanting excess waste. The comminuted ECM can be dried, for example freeze dried, to form a powder. Thereafter, if desired, the powder can be hydrated, that is, combined with water or buffered saline and optionally other pharmaceutically acceptable excipients, to form a fluid composition, e.g. having a viscosity of about 2 to about 300,000 cps at 25° C. The higher viscosity compositions can have a gel or paste consistency. This gelatinous composition can be used as fill material in and/or around an implant of the invention.

Additionally, such gelatinous or flowable materials can include solubilized and/or particulate ECM components, and in preferred forms include ECM gels having suspended therein ECM particles, for example having an average particle size of about 50 microns to about 500 microns, more preferably about 100 microns to about 400 microns. The ECM particulate can be added in any suitable amount relative to the solubilized ECM components, with preferred ECM particulate to ECM solubilized component weight ratios (based on dry solids) being about 0.1:1 to about 200:1, more preferably in the range of 1:1 to about 100:1. The inclusion of such ECM particulates in the ultimate gel can serve to provide additional material that can function to provide bioactivity to the gel (e.g. itself including FGF-2 and/or other growth factors or bioactive substances as discussed herein) and/or serve as scaffolding material for tissue ingrowth.

In additional embodiments, the present invention provides medical products that include means or devices as described herein for locating an inventive implant in a patient, and written materials including instructions for use of the means or devices to locate the implant. The products can include the means or devices packaged together with the instructions, e.g. in sterile medical packaging. Related embodiments of the invention include methods for distributing such means or devices, or otherwise conducting business, which include distributing such means or devices for locating inventive implants in a patient, and also distributing information relating the use of such means or devices for locating inventive implant in a patient. Such information can be distributed packaged with the means or device, or separately, e.g. including information or instructions available on a communication network, including a global computer communication network such as the internet.

The present invention also provides, in certain aspects, a line of medical products, wherein a medical product of the invention includes one or more devices, apparatuses or systems of the invention in a sealed package. In some forms of the invention, medical products are provided that include one or more pocket or pocket-like structures such as any of those described herein, and potentially also an electronic or other implantable medical device, enclosed within sterile medical packaging. Illustratively, such a medical product can have packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly.

Additionally, the package can include indicia to communicate the contents of the package to a person, machine, computer, and/or electronic device. Such indicia may include the dimensions of, the type of materials used to form, and/or other useful information regarding the contents of the package. In certain embodiments, the contents are packaged for sale with instructions for use. For example, in certain preferred embodiments, a medical product includes at least one inventive implant within a sterile package, wherein the packaging can have visible indicia identifying the contents as suitable for implantation in association with an electronic or other implantable medical device, and/or can contain or otherwise be associated with printed materials identifying the contents as such and including information concerning its use.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A medical product, comprising:
a remodelable material pocket having a first side wall and a second side wall opposite the first side wall, the first and second side walls defining an interior space for receiving an implantable medical device, wherein the first side wall is comprised of a first segment of sheet-form multilaminate extracellular matrix material having a plurality of extracellular material layers that have been dehydration bonded to one another by lyophilization, wherein the second side wall is comprised of a second segment of sheet form multilaminate extracellular matrix material having a plurality of extracellular material layers that have been dehydration bonded to one another by lyophilization, said first side wall and said second side wall forming exterior and interior surfaces of the pocket, with said first segment of sheet-form multilaminate extracellular matrix material providing a wall thickness of said first side wall between said exterior and interior surfaces of the pocket defined by said first side wall and said second segment of sheet form multilaminate extracellular matrix material providing a wall thickness of said second side wall between said exterior and interior surfaces of the pocket defined by said second side wall, wherein the remodelable material pocket comprises a first seam wherein a first portion of the first side wall and a first portion second side wall are sutured together on a first side of the interior space with a biodegradable suture material, and a second seam wherein a second portion of the first side wall and a second portion of the second side wall are sutured together with a biodegradable suture material on a second side of the interior space opposite the first side of the interior space, wherein the remodelable material pocket comprises an open end extending between the first seam and the second seam, wherein the open end communicates with the interior space and is dimensioned for slidable receipt of an implantable electronic medical device into the interior space, wherein the remodelable material pocket comprises a closure flap extendable over the open end, and further wherein said first segment of sheet-form multilaminate extracellular matrix material and said second segment of sheet-form multilaminate extracellular matrix material have a plurality of openings that extend therethrough; and
an implantable electronic medical device positioned in said pocket within the interior space, and wherein said first segment of sheet-form multilaminate extracellular matrix material and said second segment of sheet form multilaminate extracellular matrix material are pliable so as to be conformable to the implantable electronic medical device;
wherein said first segment of sheet-form multilaminate extracellular matrix material and said second segment of sheet-form multilaminate extracellular matrix material are effective to promote angiogenesis and cellular invasion and ingrowth therein such that upon implantation said first segment of sheet-form multilaminate extracellular matrix material and said second segment of sheet-form multilaminate extracellular matrix material break down and are replaced by new patient tissue that includes new blood vessels forming a vascularized patient tissue pouch, wherein the new patient tissue is not uncontrolled fibrotic scar tissue, and wherein said first side wall and said second side wall are free from any non-remodelable component such that following implantation a remodeled tissue structure is generated forming an all-natural patient tissue pocket that conforms to the implantable electronic medical device to provide a secure, fitted placement of the implantable electronic medical device at the implant site.

2. The medical product of claim 1, wherein said implantable electronic medical device is a cardiac rhythm management (CRM) device.

3. The medical product of claim 2, wherein said CRM device is a pacing device.

4. The medical product of claim 2, wherein said cardiac rhythm management device comprises a battery.

5. The medical product of claim 1, wherein said implantable electronic medical device has an outer surface that is non-receptive to tissue ingrowth, said outer surface positioned adjacent said remodelable material.

6. The medical product of claim 1, further comprising one or more leads extending from said implantable electronic medical device, and wherein said remodelable material pocket is configured to allow said leads to extend from said implantable electronic medical device to a location exterior of said remodelable material pocket.

7. The medical product of claim 1, wherein the extracellular matrix material comprises serosa, pericardium, submucosa, dura mater, peritoneum, or dermal collagen.

8. A method of treating a patient, comprising:
providing a remodelable material pocket implanted in a patient with an implantable electronic medical device positioned in the pocket, wherein said remodelable material pocket having a first side wall and a second side wall opposite the first side wall, wherein the first side wall is comprised of a first segment of a sheet-form extracellular matrix material having a plurality of extracellular material layers that have been dehydration bonded to one another by lyophilization, wherein the second side wall is comprised of a second segment of sheet-form multilaminate extracellular matrix material having a plurality of extracellular material layers that have been dehydration bonded to one another by lyophilization, said first side wall and said second side wall forming interior and exterior surfaces of the pocket and a first segment of sheet-form multilaminate extracellular matrix material providing a wall thickness of said first side wall between said interior and exterior surfaces of the pocket defined by said first side wall and said second segment of sheet form multilaminate extracellular matrix material providing a wall thickness of said second side wall between said exterior and interior surfaces of the pocket defined by said second side wall, wherein said first segment of sheet-form multilaminate extracellular matrix material and said second segment of sheet-form multilaminate extracellular matrix material are effective to promote angiogenesis and cellular invasion and ingrowth therein such that upon implantation said first segment of sheet-form multilaminate extracellular matrix material and said second segment of sheet-form multilaminate extracellular matrix material break down and are replaced by new patient tissue such that a remodeled tissue structure is generated forming a vascularized patient tissue pouch around the implantable electronic medical device wherein the vascularized patient tissue pouch is not uncontrolled fibrotic scar tissue, wherein said remodelable material pocket is fully remodelable and comprises seams between said first side wall and said second side wall that are sutured with biodegradable suture material, wherein the remodelable material pocket comprises an open end dimensioned for slidable receipt of the implantable medical device within an interior space defined by the interior surfaces of the first side wall and the second side wall, and wherein the remodelable material pocket comprises a closure flap extended over the open end, wherein the closure flap comprises a portion of the first side wall, and wherein the closure flap is sutured to the second side wall, wherein the first segment of sheet-form multilaminate extracellular matrix material and the second segment of sheet-form multilaminate extracellular matrix material have a plurality of openings that extend therethrough, and wherein said first segment of sheet-form multilaminate extracellular matrix material and said second segment of sheet-form multilaminate extracellular matrix material are pliable so as to be conformable to the implantable electronic medical device.

9. The method of claim 8, wherein said providing includes placing a material between the implantable medical device and an interior surface of said pocket.

10. The method of claim 9, wherein said material is a gel coating that coats said interior surface.

11. The method of claim 9, wherein said material includes a drug.

12. The method of claim 8, wherein the remodelable material pocket is implanted in a sub-muscular location.

13. A method of treating a patient, comprising:
providing a remodelable pocket construct having a first side wall and a second side wall opposite the first side wall, the first and second side walls defining an interior space for receiving an implantable medical device, wherein the first side wall is comprised of a first segment of sheet-form multilaminate extracellular matrix material having a plurality of extracellular material layers that have been dehydration bonded to one another by lyophilization, wherein the second side wall is comprised of a second segment of sheet form multilaminate extracellular matrix material having a plurality of extracellular material layers that have been dehydration bonded to one another by lyophilization, the first side wall and the second side wall forming exterior and interior surfaces of the pocket, with the first segment of sheet-form multilaminate extracellular matrix material providing a wall thickness of the first side wall between the exterior and interior surfaces of the pocket defined by the first side wall and the second segment of sheet form multilaminate extracellular matrix material providing a wall thickness of said second side wall between said exterior and interior surfaces of the pocket defined by said second side wall, wherein the remodelable pocket comprises an open end dimensioned for slidable receipt of an implantable medical device within the interior space;
positioning an implantable electronic medical device within the interior space of the remodelable pocket construct, wherein said sheet-form multilaminate remodelable extracellular matrix material is pliable so as to be conformable to the implantable electronic medical device;
closing the open end of the remodelable pocket construct by securing a portion of the first side wall to a portion of the second side wall;
creating an opening in the skin of a patient to provide access to a subcutaneous body location; and
positioning in the subcutaneous body location the remodelable pocket construct containing the implantable electronic medical device, wherein the remodelable extracellular matrix material is effective upon implantation to promote angiogenesis and cellular invasion and ingrowth into the pocket construct and to become replaced by new vascularized patient tissue so that an all-natural remodeled tissue pocket structure comprising newly generated vascularized patient tissue that conforms to the implantable electronic medical device to provide a secure, fitted placement of the implantable electronic medical device at the subcutaneous body location.

14. The method of claim 13, wherein said electronic medical device has an outer surface that is non-receptive to tissue ingrowth.

15. The method of claim 14, wherein the electronic medical device is a cardiac rhythm management device.

* * * * *